(12) United States Patent
Thiel (10) Patent No.: US 8,577,212 B2
(45) Date of Patent: Nov. 5, 2013

(54) HANDHELD DENTAL CAMERA AND METHOD FOR CARRYING OUT OPTICAL 3D MEASUREMENT

(75) Inventor: Frank Thiel, Ober-Ramstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 130 days.

(21) Appl. No.: 13/213,893

(22) Filed: Aug. 19, 2011

(65) Prior Publication Data
US 2012/0075425 A1    Mar. 29, 2012

Related U.S. Application Data

(63) Continuation of application No. PCT/EP2010/052241, filed on Feb. 23, 2010.

(30) Foreign Application Priority Data

Feb. 23, 2009   (DE) .................. 10 2009 001 086

(51) Int. Cl.
    *A61B 1/04*   (2006.01)
(52) U.S. Cl.
    USPC .............................................. 396/16; 348/46
(58) Field of Classification Search
    USPC .............................................. 396/16; 348/46
    See application file for complete search history.

(56) References Cited

U.S. PATENT DOCUMENTS

| | | |
|---|---|---|
| 3,013,467 A | 12/1961 | Minsky |
| 5,790,242 A | 8/1998 | Stern et al. .................. 356/4.04 |
| 6,019,721 A | 2/2000 | Holmes et al. |
| 6,263,234 B1 * | 7/2001 | Engelhardt et al. ........... 600/476 |
| 6,327,041 B1 | 12/2001 | Guern .......................... 356/601 |
| 6,697,164 B1 | 2/2004 | Baybayoff et al. |

(Continued)

FOREIGN PATENT DOCUMENTS

| | | |
|---|---|---|
| CA | 2334225 | 12/1999 |
| DE | 3 428 593 C2 | 11/1988 |

(Continued)

OTHER PUBLICATIONS

Tiziani, H.J. et al., "Three-dimensional image sensing by chromatic confocal microscopy", Applied Optics, vol. 33, No. 10, Apr. 1, 1994, pp. 1838-1843.

(Continued)

*Primary Examiner* — W B Perkey
*Assistant Examiner* — Fang-Chi Chang
(74) *Attorney, Agent, or Firm* — Fitzpatrick, Cella, Harper & Scinto (57) ABSTRACT

A handheld dental camera performs three-dimensional, optical measurements. The camera includes a light source that emits an illuminating beam, a scanning unit, a color sensor, and a deflector. The scanning unit focuses the illuminating beam onto a surface of an object to be measured. The surface of the object reflects the illuminating beam and forms a monitoring beam, which is detected by the color sensor. Focal points of wavelengths of the illuminating beam form chromatic depth measurement ranges. The scanning unit stepwise displaces the chromatic depth measurement ranges by a step width smaller than or equal to a length of each chromatic depth measurement range, so that a first chromatic depth measurement range in a first end position of the scanning unit and a second chromatic depth measurement range in a second end position are precisely adjoined in a direction of a measurement depth, or are partially overlapped.

19 Claims, 2 Drawing Sheets

(56) References Cited

U.S. PATENT DOCUMENTS

| | | | |
|---|---|---|---|
| 7,986,415 B2 | 7/2011 | Thiel et al. | |
| 2004/0156626 A1* | 8/2004 | Thoms | 396/17 |
| 2007/0086762 A1* | 4/2007 | O'Keefe et al. | 396/16 |
| 2009/0279103 A1 | 11/2009 | Thiel et al. | |
| 2010/0020329 A1 | 1/2010 | Lehmann | |
| 2011/0080576 A1* | 4/2011 | Thiel et al. | 356/73 |
| 2011/0221879 A1* | 9/2011 | Schmidt | 348/77 |

FOREIGN PATENT DOCUMENTS

| | | |
|---|---|---|
| DE | 103 21 885 A1 | 12/2004 |
| DE | 10 2004 049 541 A1 | 4/2006 |
| DE | 699 28 453 T2 | 8/2006 |
| DE | 10 2006 026 775 A1 | 12/2007 |
| DE | 10 2007 005 625 A1 | 8/2008 |
| DE | 10 2007 005 726 A1 | 8/2008 |
| EP | 0 997 748 A2 | 5/2000 |
| EP | 0 762 143 B1 | 10/2000 |
| GB | 2 144 537 A | 3/1985 |
| WO | 2005/116578 A2 | 12/2005 |

OTHER PUBLICATIONS

Ruprecht, A. K. et al., "Chromatic confocal detection for high speed micro-topography measurements," Electronic Imaging, Proceedings of SPIE, vol. 5302-6, Jan. 2004, pp. 53-60.

Schmoll, J., "3D-Spektrofotometrie," University of Potsdam, Jun. 2001, pp. 12 and 13 (and an English translation thereof).

German Patent Office, Official Communication dated Mar. 31, 2010, 4 pages (and machine-generated English translation thereof).

European Patent Office, Internationaler Recherchenbericht dated Jul. 14, 2010, in connection with International Application No. PCT/EP2010/052241, 5 pages (and an English translation thereof entitled International Search Report).

International Bureau of the World Intellectual Property Office, "Internationaler Vorlaufiger Uber Die Patentierbarkeit," in connection with International Application No. PCT/EP2010/052241, completed Jun. 15, 2011 (and English translation thereof entitled International Preliminary Report on Patentability).

* cited by examiner

HANDHELD DENTAL CAMERA AND METHOD FOR CARRYING OUT OPTICAL 3D MEASUREMENT

RELATED APPLICATIONS

This application is a continuation of International Application PCT/EP2010/052241, filed Feb. 23, 2010, claims benefit of the filing date of that application under 35 U.S.C. §120, and claims benefit under §119 of German Application No. 10 2009 001 086.6, filed Feb. 23, 2009. The entire contents of those two applications are incorporated herein by reference.

TECHNICAL FIELD

The invention relates to a handheld dental camera for carrying out optical 3D measurement using a confocal measuring method, which handheld dental camera comprises a chromatic objective, a polychromatic light source, and a color sensor, and also to a method for using the dental camera of the invention.

PRIOR ART

Confocal microscopy is well-known in the prior art and is disclosed, inter alia, in the patent specification U.S. Pat. No. 3,013,467.

The chromatic confocal measuring method provides the possibility of effecting focusing without the need for mechanically moving components, and as a result usually reduce measuring time significantly, as was proposed by G. Molesini in 1983 in conjunction with a spectrometer (GB 2144537 and DE 3428593 C2). An example of successful application of the chromatic confocal measuring method is described by H. J. Tiziani and H.-M. Uhde in the professional article "Three-dimensional image sensing by chromatic confocal microscopy" in Applied Optics, Vol. 33, No. 1, April 1994, pp. 1838 to 1843. In this case, the spectral analysis is performed by means of three color filters. Thus the depth measurement range and the depth resolution achievable in this application are limited.

The patent specification DE 103 21 885 AI discloses a chromatic confocal system comprising a component having variable refractive power, for example, a diffractive component. In the optical arrangement shown in FIG. 2 of said patent specification, a series of micro-lenses is provided for illumination in order to obtain the confocal signals via the wavelength, and, for analysis, a spectrometer comprising an area scan camera is disposed downstream so that line profiles can be obtained from a single planar camera image by means of a line spectrometer. In the publication "Chromatic confocal detection for speed micro-topography measurements" by A. K. Ruprecht, K. Koerner, T. F. Wiesendanger, H. J. Tiziani, W. Osten in Proceedings of SPIE, Vol. 5302-6, pp. 53-60, 2004, FIG. 4 shows a chromatic confocal line sensor for topographic measurement. In this case, in order to obtain the confocal signals via the wavelength, a line spectrometer is disposed downstream of the chromatic confocal system so that line profiles of the surface of an object can be ascertained from a single camera image using a single area scan camera and a line spectrometer. The use of a spectrometer basically allows for higher spectral resolution compared with an arrangement comprising three color filters or an RGB color camera or even a four channel color camera and is thus more advantageous.

On pages 12 and 13 of the dissertation entitled "3D-Spektrofotometrie extragalaktischer Emissionslinien" [3D-Spectrophotometry of extragalactic emission lines] by J. Schmoll, submitted to the University of Potsdam in June 2001, lenticular direct coupling is described, which was first applied in the TIGER spectrograph by Courtes et al. in 1988. In said citation, the lenticular raster is rotated through an angle counter to the direction of dispersion. Because of the shift of adjacent spectra, this technique has the reputation of being complicated for evaluation purposes, and the area of the area sensor is not utilized economically, because the filling factor is low. In scientific papers, terms such as 3D-spectrophotometry and imaging spectroscopy and integral-field spectrophotometry are also used in this connection.

The chromatic confocal measuring method has the advantage that the camera can, in principle, be one not having any mechanically moving components, and that the data rate is low, since only a single color spectrum needs to be recorded for any one measuring point.

However, the disadvantage of the chromatic confocal measuring method is that a spectral broadband light source must be used that has a wavelength spectrum that is as broad and continuous as possible. Therefore, primarily halogen lamps and xenon gas-discharge lamps are suitable for use as the light source. These light sources are comparatively unwieldy and large, due to their design. A compact light source such as a laser diode or a super-luminescent diode is less suitable for the chromatic confocal measuring method, since it typically has a rather narrow wavelength spectrum. The depth measurement range is therefore greatly restricted and not suitable for measuring relatively large objects such as teeth.

In a classical scanning confocal measuring method with mechanical depth measurement, the position of a single focal point is moved by mechanically moving individual lens elements of the optical system or by moving the entire optical system relatively to the object. The light source used is one that has the narrowest possible wave spectrum in order to keep the area of the focal point small. For scanning a single measuring point, the optical system must thus be mechanically moved, in steps, over the entire measurement depth, a data set being acquired for each position of the optical system and an elevation value then determined from all of the data sets acquired. The resolution of the elevation values depends on the width of the individual mechanical steps carried out for moving the optical system. Therefore, the classical scanning confocal measuring method suffers from the shortcoming that very large amounts of data accumulate that have to be processed for the purpose of carrying out good resolution.

The classical scanning confocal measuring method has the advantage that compact light sources such as LEDs and LDs can be used that have a narrow-band wavelength spectrum.

The object of this invention is to provide a confocal apparatus and a confocal method that makes it possible to carry out rapid optical 3D measurement of the object to be measured, in which confocal method it is possible to use a compact light source and the data rates are low.

SUMMARY OF THE INVENTION

This object is achieved by means of the handheld dental camera of the invention and the method of the invention.

The handheld dental camera of the invention for carrying out optical 3D measurement comprises a chromatic objective, a polychromatic light source, and a color sensor, in which handheld dental camera the polychromatic light source emits an illuminating beam (8) that can be focused, at least in terms of one wavelength thereof, onto the surface of an object of interest by means of the chromatic objective. The illuminating beam is reflected by the surface to form a monitoring beam, which is capable of being detected by means of the color sensor. The focal points of the various wavelengths of the illuminating beam form a chromatic depth measurement range.

The handheld dental camera further comprises an movable scanning unit comprising at least the chromatic objective. The chromatic depth measurement range can be moved in steps by means of the scanning unit so that at least a second chromatic depth measurement range in a second position of the scanning unit adjoins a first chromatic depth measurement range in a first position of the scanning unit or at least partly overlaps the first chromatic depth measurement range. In this manner, an enlarged overall depth measurement range is formed from the at least two different depth measurement ranges.

The handheld dental camera for carrying out optical 3D measurement can be a handheld camera that is particularly suitable for producing dental intraoral images of teeth and that combines the principles of chromatic confocal depth measurement and scanning confocal depth measurement.

In the chromatic confocal measuring method, the measurement is carried out without mechanically moving the optical system in that the focal points of different wavelengths are distributed over the entire measurement depth and use is made of spectral analysis to ascertain the wavelength of which the focal point is located on the surface. The focal position, that is, the z coordinate of the object surface can be ascertained from this wavelength. The resolution of the z coordinate depends primarily on the continuous distribution of wavelengths in the spectrum of the illuminating beam used, and on the precision of the spectral analysis used.

For this purpose, a polychromatic light source is used, of which the spectral range emitted in the form of the illuminating beam has a plurality of wavelengths. This illuminating beam is focused by means of a chromatic objective onto the object to be measured. Since a chromatic objective intensifies the effect of chromatic aberrations, the focal points for the different wavelengths of the illuminating beam are kept well apart. The focal points of the shortest and longest wavelengths of the spectral range of the illuminating beam can be spaced from each other by up to 5 mm, and they form the chromatic depth measurement range of the handheld dental camera. An elevation value can be assigned to each wavelength within this chromatic depth measurement range.

As a result of this separation of the focal points, only the focal point of a single wavelength or at least a very narrow wavelength range of the spectral range of the illuminating beam is located exactly on the surface of the object of interest, and this wavelength dominates the spectral intensity profile of the monitoring beam.

The monitoring beam is detected by means of a color sensor capable of detecting a broad spectral range and of differentiating the individual wavelengths. A spectrometer or a CCD sensor is suitable for this purpose.

Thus that wavelength of the monitoring beam that has the maximum intensity can be ascertained, and an elevation value corresponding to this wavelength can be assigned to the measuring point on the surface as long as the measuring point is located within the chromatic depth measurement range.

In the present invention, use is made of compact polychromatic light sources such as LEDs, laser diodes (LDs), and super-luminescent diodes (SLDs), of which the wavelength spectrum is narrow compared with halogen lamps or xenon gas-discharge lamps. In order to still make it possible to measure a sufficiently large depth measurement range, the chromatic confocal measuring method is combined with the classical scanning confocal measuring method.

In the scanning confocal measuring method, a single focal point is moved along the measurement depth by mechanically moving the optical system stepwise, and the detected intensities of the monitoring beam are used to identify that step of the mechanical movement of the optical system in which the focal point is located exactly on the surface of the object to be measured. The focal position can then be ascertained from the step in which a maximum intensity of the illuminating beam is detected. The resolution of the z coordinate, i.e. the elevation value, is ascertained in this method by means of the step width of the mechanical movement of the optical system.

By means of the scanning unit in the handheld dental camera, which scanning unit comprises at least the chromatic objective, the plurality of focal points that are kept apart by the use of the polychromatic light source and the chromatic objective can be moved at the same time over the depth measurement range. The step width can be such that it is equal, as precisely as possible, to the length of the chromatic depth measurement ranges. Thus it is possible for several chromatic depth measurement ranges that adjoin or overlap each other along the z axis to be measured successively and a 3D data set to be acquired for an enlarged overall depth measurement range from the data sets thus acquired. This enlarged depth measurement range is given by the sum of the chromatic depth measurement ranges that adjoin or overlap each other. For example, a chromatic depth measurement range that can be achieved by means of a compact light source such as an LED, LD, or SLD can have a length of 0.5 mm. If an overall depth measurement range of 20 mm is to be measured, this measurement can be carried out in 40 steps having a step width of 0.5 mm.

It is thus possible, in spite of a narrow chromatic depth measurement range, to achieve a measurement depth that makes it possible to scan an object such as a tooth.

One advantage of the handheld dental camera of the invention over the purely chromatic confocal method is the ability to use more compact light sources such as LEDs, LDs, and SLDs, since a narrower spectral range $\Delta\lambda$ is sufficient. It is therefore possible to dispense with the unwieldy and large light sources such as halogen lamps and xenon gas-discharge lamps that are used typically in the chromatic confocal measuring method.

A further advantage of the handheld dental camera of the invention is that the number of mechanical steps required for moving the scanning unit is significantly smaller than in the purely scanning confocal method and thus the amount of data to be processed is also significantly reduced.

Advantageously, the scanning unit can be moved to exactly two positions, namely, from one end position directly to another end position.

As a result, it is possible to measure a depth measurement range that is twice as large as that possible using a purely chromatic confocal method, and the mechanical movement of the scanning unit is simpler than in the classical scanning confocal method since the scanning unit moves to only two positions that can each be defined by means of end stops.

Advantageously, the handheld dental camera comprises a deflector, which is disposed between the chromatic objective and the object to be measured, the illuminating beam being deflectable by the deflector in a direction extending at right angles to the longitudinal axis of the handheld dental camera toward the object to be measured.

The deflector can be a prism or a mirror that is disposed at a fixed angle of 45° relative to the illuminating beam so that the illuminating beam is deflected at an angle of 90° toward the object of interest. Thus the handheld dental camera of the invention can be of a very compact design and it can enable intraoral images to be collected from an awkward position in the oral cavity of the patient.

Advantageously, the light source can be a halogen lamp or a xenon gas-discharge lamp having a wavelength spectrum ranging from 500 nm to 2000 nm.

Thus a broad wavelength spectrum is provided so that the chromatic depth measurement range will be larger and the required overall depth measurement range will be covered in only a few steps. Since halogen lamps and xenon gas-discharge lamps are too large to be integrated in a compact handheld dental camera, they can be connected to the handheld dental camera by, say, a fiber-optic light guide.

Advantageously, the light source can be a super-luminescent diode (SLD).

A super-luminescent diode (SLD) is a diode that has a relatively broad wavelength spectrum and output power comparable to that of laser diodes and showing extremely low spectral noise.

The use of an SLD has the advantage that it can be integrated in a handheld dental camera due to its compact design, while a relatively broad wavelength spectrum is provided in spite of its compactness.

Advantageously, the super-luminescent diode (SLD) can have a spectrum having a wavelength ranging from 900 nm to 1000 nm.

There are different types of super-luminescent diodes having different wavelength ranges. The SLD having a wavelength range of from 900 nm to 1000 nm has a relatively constant intensity at all wavelengths. The color sensor used must be chosen according to the wavelength-dependent intensity profile such that the wavelength-dependent detection efficiency is not reduced to zero.

Advantageously, the super-luminescent diode (SLD) can have a spectrum having a wavelength ranging from 1500 nm to 1650 nm.

Thus a broader wavelength spectrum is provided, as a result of which the number of mechanical scanning steps can be reduced.

Advantageously, the light source can be a white-light LED.

On account of its compactness, a white-light LED can be integrated in a handheld dental camera, and the broader spectrum of a white-light LED makes it possible to reduce the number of mechanical scanning steps.

Advantageously, the chromatic depth measurement range can have a length of from 0.5 mm to 5 mm.

Thus the handheld dental camera of the invention is particularly suitable for scanning teeth. Therefore, for example, an overall depth measurement range of 30 mm can be measured in only six steps of 5 mm each.

Advantageously, the handheld dental camera comprises a data processing unit or a connector to which a data processing unit can be connected. By means of the data processing unit, it is possible to acquire data and produce a data set for each chromatic depth measurement range. These different data sets can then be combined to form an overall 3D data set for the total depth measurement range.

Thus the handheld dental camera can be of compact design and capable of covering a depth measurement range that makes it possible to measure an entire tooth.

Advantageously, the scanning unit can be moved mechanically at a frequency ranging from 1 Hz to 1000 Hz.

Thus the surface of the object of interest can be scanned in a relatively short period of time. When use is made of a handheld camera, it is particularly important that the intervals between exposures be as short as possible, since a user cannot hold the camera steadily for more than very short periods of time.

Advantageously, a pivotal mirror is disposed between the light source and the surface of the object so that the illuminating beam can be moved, in steps, in the lateral direction over the entire surface of the object of interest by stepwise tilting of the pivotal mirror.

Depending on the embodiment, there is provided either a pattern that entirely covers the surface of the object to be measured, or a line, or a single dot in the xy plane to serve as the illuminating beam. In the case of a line, this must be moved stepwise across the object in a direction at right angles to the line, and an image must be produced at each step so that the individual data sets can then be combined to form a data set for the entire object of interest. Similarly, an illuminating beam in the form of a dot must be moved stepwise across the object in the x and y directions, and the individual data sets can then be combined to form an overall data set of the object of interest.

It is a further object of the invention to provide a method for carrying out optical 3D measurement, in which method an illuminating beam emitted by a polychromatic light source is focused, at least in terms of one wavelength thereof, by a chromatic objective onto the surface of an object to be measured, and the illuminating beam reflected by the surface to form a monitoring beam is detected by a color sensor. The focal points of the different wavelengths of the illuminating beam form a chromatic depth measurement range. A scanning unit comprising at least the chromatic objective is moved stepwise such that at least a second chromatic depth measurement range in a second position of the scanning unit adjoins or partly overlaps a first chromatic depth measurement range in a first position of the scanning unit. In this way, an enlarged overall depth measurement range is formed from the at least two depth measurement ranges.

One advantage of the method of the invention is that scanning is carried out more rapidly than in the classical scanning method, since the scanning unit is mechanically moved, not continuously but only between a few, at least two, predetermined positions.

A further advantage of the method of the invention is that lower data rates occur which can be analyzed using existing methods in a relatively short period of time.

Advantageously, the scanning unit is moved just once from one end position directly to another end position.

As a result, a depth measurement range can be measured that is larger than that possible in a purely chromatic confocal method, and the movement of the scanning unit can be carried out more simply than is possible in the classical scanning confocal method, since the scanning unit moves only to two positions that can each be defined by with end stops.

Advantageously, the illuminating beam is deflected by a deflector toward the object of interest.

Thus the direction of the illuminating beam is adjusted in a simple manner, for example by means of a deflection mirror.

Advantageously, a light source having a spectral range of from 300 nm to 2000 nm is used.

Thus a relatively large chromatic depth measurement range can be scanned in a single step so that only a few steps are required for measuring the entire object.

Advantageously, a light source having a spectral range of from 900 nm to 1000 nm or from 1500 nm to 1650 nm is used.

In this case, it would be necessary to carry out more steps for measuring the entire object, but compact light sources such as LEDs, LDs and SLDs can be used.

Advantageously, focal points for the different wavelengths are enlarged so that a chromatic depth measurement range having a length of from 0.5 mm to 5 mm may be achieved.

Thus fewer steps need to be carried out for movement of the scanning unit, which makes it possible to scan the object of interest more rapidly.

Advantageously, a data set is ascertained for each chromatic depth measurement range, the data sets being saved in the handheld dental camera and then combined to form a 3D data set of the object of interest or transmitted to a data processing unit.

If only small quantities of data are to be processed, it is possible to reduce the data-transmission time by processing these data within the camera. In the case of larger quantities of data, it may be advantageous to carry out the data processing externally of the camera.

Advantageously, the scanning unit can be moved at a frequency ranging from 1 Hz to 1000 Hz.

Thus the surface of the object to be measured can be measured in a relatively short period of time, and an appropriate handheld dental camera can therefore be held in the hand in order to carry out a measuring process.

Advantageously, the illuminating beam is moved in the lateral direction across the entire surface of the object of interest by stepwise tilting of a pivotal mirror.

As a result, the entire object of interest can be scanned even when the illuminating beam is incident upon the object only in the form of a dot or a line.

Advantageously, the movement of the scanning unit for the purpose of measuring the individual chromatic measuring regions giving the total measuring region is carried out in a number of steps. Then the scanning unit is moved back to its first position in an additional step, and this scanning cycle of the scanning unit is repeated until the measuring procedure is complete.

Thus the illuminating beam is moved, in steps, from a top end of the total depth measurement range to a bottom end of the total depth measurement range and back to its original position at the top end of the total depth measurement range for the purpose of measuring the next adjacent measuring point. This scanning cycle provides more rapid measurement of the entire surface.

Advantageously, the movement of the scanning unit for the purpose of measuring the individual chromatic measuring regions giving the total measuring region is carried out in a number of steps. Then the scanning unit is moved back, in steps, to its first position, and this scanning cycle of the scanning unit is repeated until the measuring procedure is complete.

This scanning cycle omits the step in which the illuminating beam is moved back to its original position, so that the duration of the scanning procedure is shortened.

BRIEF DESCRIPTION OF THE DRAWINGS

Exemplary embodiments of the invention are shown in the drawings, in which.

EXEMPLARY EMBODIMENTS

Figure 1:
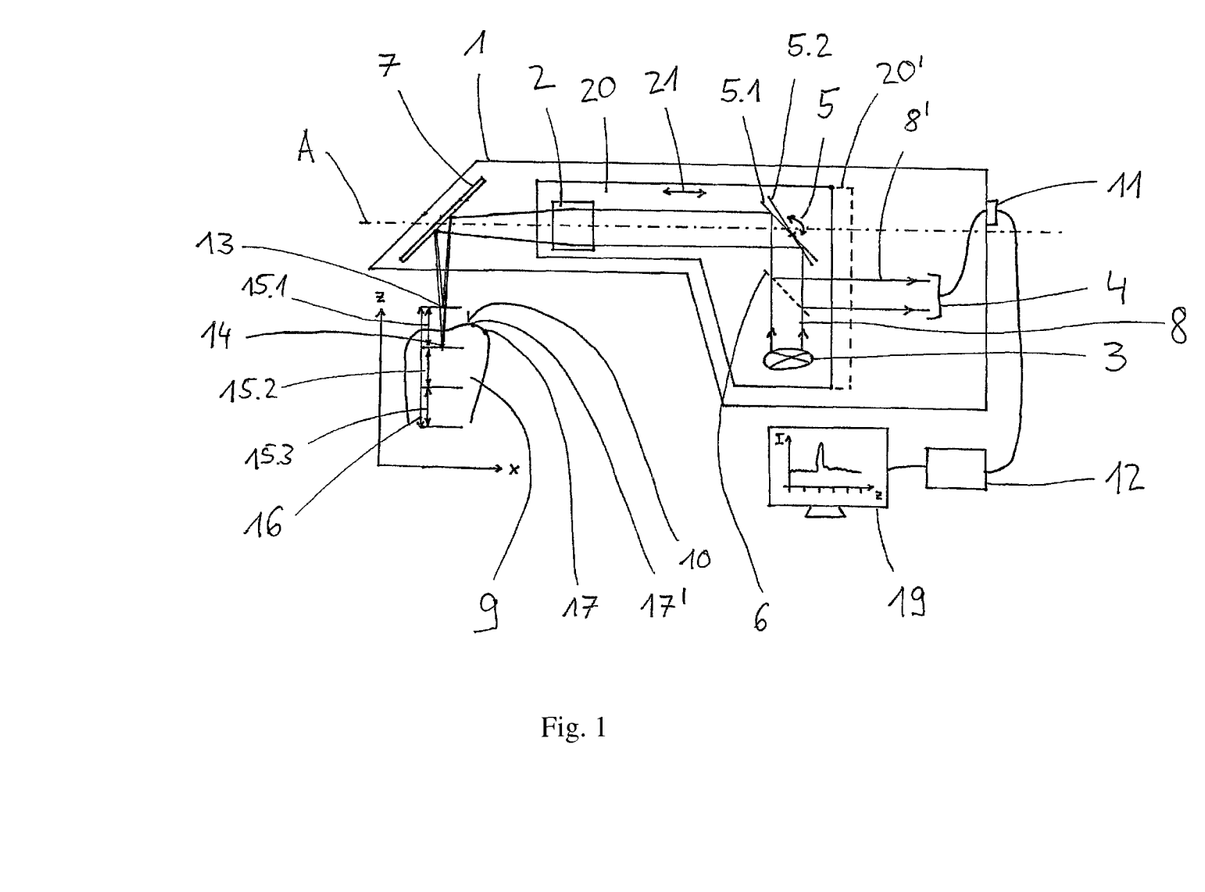
FIG. 1 shows a handheld dental camera.

FIG. 1 shows an exemplary embodiment of a handheld dental camera 1 of the invention for carrying out 3D measurements. The handheld dental camera 1 comprises a scanning unit which, in this exemplary embodiment, comprises a chromatic objective 2, a polychromatic light source 3, a pivotal mirror 5, and a beam splitter 6, and which is capable of being moved along the longitudinal axis A within the handheld dental camera 1. The handheld dental camera 1 further comprises a color sensor 4, a deflector 7, for example a deflection mirror, and a connector 11 to which a data processing unit 12 can be connected.

The polychromatic light source 3 emits an illuminating beam 8 that passes through the beam splitter 6, for example, a semi-transparent mirror or a beam splitter prism, with as little obstruction as possible, and is deflected by the pivotal mirror 5 toward the chromatic objective 2. The illuminating beam 8 is focused by the chromatic objective and deflected by the deflector 7 toward the object 9 of interest, such as a tooth. The surface 10 of the object 9 of interest reflects a portion of the illuminating beam 8 back into the handheld dental camera 1 in the form of a monitoring beam 8'. The monitoring beam 8' is deflected by the deflector 7 toward the chromatic objective 2, and it passes through the chromatic objective 2, and is deflected by the pivotal mirror 5 toward the beam splitter 6, and is deflected to a maximum extent by the beam splitter 6 toward the color sensor 4, such as a CCD sensor. The image data recorded by the CCD sensor are transferred by way of the connector 11 to a data processing unit 12 in the form of a PC.

The method for carrying out optical 3D measurement of the invention comprises both elements of a chromatic confocal measuring method and elements of a scanning confocal measuring method.

The polychromatic light source 3 has a spectral range of two or more wavelengths. The illuminating beam emitted by the light source 3 thus has at least two wavelengths differing from each other. Primarily, a compact polychromatic light source such as an LED, a laser diode (LD) or a super-luminescent diode (SLD) can be used as the polychromatic light source for the handheld dental camera 1 of the invention. Halogen lamps or xenon gas-discharge lamps can also be used as the light source. However, these lamps, due to their size, are only suitable for the handheld dental camera 1 of the invention when they are not disposed inside the camera 1 itself but are instead connected thereto by means of a fiber-optic light guide.

The beam splitter 6 is a semi-transparent optical element that allows the illuminating beam to pass through, at least partially, without any obstruction and deflects the monitoring beam, at least partially, toward the color sensor for the purpose of detection.

The pivotal mirror 5 is a mirror that is mounted for rotation about at least one axis and is angularly adjusted by means of an electric motor in a computer-controlled manner. The illuminating beam 8 can be moved over the entire object 9 of interest by tilting the mirror into different positions 5.1, 5.2 in order to make it possible to determine an elevation value, i.e. a z value, for all points 17, 17' in the xy plane of the object 9 of interest, and to combine the same to form a 3D data set of the object 9 of interest.

The chromatic objective 2 is an optical element that intensifies the effect of chromatic aberrations such that the focal points for the different wavelengths of the illuminating beam 8 are kept clearly apart. This results in a chromatic depth measurement range 15.1 that extends from the position of a first focal point 13 located closest to the chromatic objective 2 to the position of a second focal point 14 located farthermost from the chromatic objective 2. Within this chromatic depth measurement range 15.1, it is possible to acquire an elevation value. The measuring accuracy depends on the distance between the intermediate focal points of the additional wavelengths present in the illuminating beam 8.

The scanning unit 20 is a unit that is moved in the direction of the arrow 21 within the handheld dental camera 1 along the longitudinal axis A of the handheld dental camera 1, for example, by means of an electronically controlled electric motor, so that the focal points 13, 14 of the illuminating beam 8 are moved along the z axis, i.e. along the depth measurement range 15.1 at right angles to the longitudinal axis A of the handheld dental camera 1. Thus, after a first depth measurement range 15.1 has been acquired by the scanning unit in a first position, the latter is moved to a second position 20', as a result of which the focal points 13, 14 are moved to such an extent that the position of the focal point 13 in the second position of the scanning unit corresponds to that of the focal point 14 in the first position of the scanning unit. Thus the depth measurement range 15.2 in the second position of the scanning unit adjoins the depth measurement range in the first position of the scanning unit. Accordingly, additional depth measurement ranges 15.3 can be added to the depth measurement range 15.2 by moving the scanning unit to additional positions along the longitudinal axis A of the handheld dental camera 1.

The color sensor 4 is a light-sensitive sensor that is capable of detecting a wavelength spectrum and of reproducing the intensity of the individual wavelength. Thus a wavelength-dependent intensity profile of the monitoring beam 8 and thus the wavelength having the maximum intensity is ascertained, from which the elevation value, that is, the z value can be computed. In the embodiment shown, the color sensor is a CCD sensor. The color sensor could alternatively be in the form of a spectrometer. The color sensor 4 is connected by means of a connector 11 to a data processing unit 12, for example, a computer and an output unit 19. Thus the data sets successively acquired for different chromatic depth measurement ranges 15.1-4 in different positions of the scanning unit 20 are saved and combined to form an overall 3D data set of the object of interest over the total depth measurement range 16.

Figure 2:
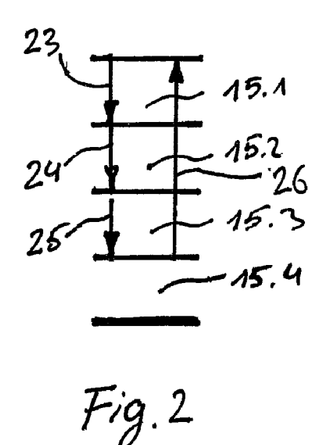
FIG. 2 is a first diagram of a measuring sequence

FIG. 2 is a diagram illustrating a cycle carried out for moving the scanning unit 20 in a plurality of steps. After the first chromatic measurement range 15.1 has been measured, the focal points between the outer focal points 13 and 14 are moved in a first step 23 toward the second chromatic depth measurement range 15.2. After the measurement of the second chromatic depth measurement range 15.2, has been completed, the focal points are moved, in a second step 24, toward the third chromatic depth measurement range 15.3. After the third chromatic depth measurement range 15.3 has been measured, the focal points are moved in a third step 25 toward the fourth chromatic depth measurement range 15.4. In a fourth step 26, the scanning unit 20 is moved back to its original position, so that the focal points 13 and 14 again include the first chromatic depth measurement range 15.1.

Typically, the entire region of the xy plane to be measured is scanned between the individual steps of the described measurement cycle for the respective depth measurement ranges 15.1, 15.2, 15.3, 15.4 adjusted in the z direction in that the illuminating beam is moved, in steps, in the x direction and/or the y direction by stepwise tilting the pivotal mirror 5. Thus the said cycle for moving the chromatic depth measurement range will typically run only once for the purpose of measuring any one object.

There is the alternative possibility of running the said measuring cycle just once for each point of interest in the xy plane, i.e. for each position 5.1, 5.2 of the pivotal mirror 5.

Figure 3:
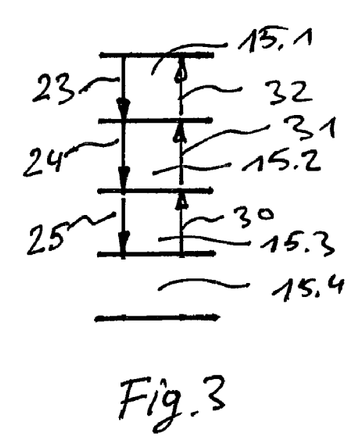
FIG. 3 is a second diagram of a measuring sequence.

If this variant is selected, the scanning cycle described can be altered to the effect that, as shown in the plurality of steps in FIG. 3 in the form of a diagram illustrating an alternative movement cycle of the scanning unit, the first three steps 23, 24, and 25 can be carried out as described with reference to FIG. 2. But in the fourth step 30, the focal points can be moved from the fourth chromatic depth measurement range 15.4 to the third chromatic depth measurement range 15.3, and to the second depth measurement range 15.2 in a fifth step 31 after measuring the third depth measurement range 15.3, and to the first depth measurement range 15.1 in a final sixth step 32 after measuring the second depth measurement range 15.2. The movement of the chromatic depth measurement ranges in the first three steps 23, 24, and 25 is carried out for the purpose of measuring a measuring point 17 shown in FIG. 1, the illuminating beam 8 then being moved in the lateral direction by tilting the pivotal mirror 5 so that the movement of the chromatic depth measurement ranges in the fourth, fifth, and sixth steps 30, 31, and 32 is carried out for the purpose of measuring an adjacent measuring point 17' shown in FIG. 1. This scanning cycle of the illuminating beam is repeated until measurement of the surface 10 is complete.

LIST OF REFERENCE NUMERALS OR CHARACTERS 1 handheld dental camera
2 objective
3 light source
4 color sensor
5 pivotal mirror
5.1 position
5.2 position
6 beam splitter
7 deflector
8 illuminating beam
8' monitoring beam
9 object to be measured
10 surface
11 connector
12 data processing unit
13 focal point
14 focal point
15.1 chromatic depth measurement range
15.2 chromatic depth measurement range
15.3 chromatic depth measurement range
15.4 chromatic depth measurement range
16 overall depth measurement range
17 measuring point
17' measuring point
18 distance
19 display device
20 scanning unit
20' scanning unit in a second position
21 direction of motion of the scanning unit
23 step
24 step
25 step
26 step
30 step
31 step
32 step

The invention claimed is:
1. A handheld dental camera that performs three-dimensional (3D), optical measurements, the camera comprising:
a polychromatic light source that emits an illuminating beam;

a scanning unit that includes a chromatic objective that focuses the illuminating beam, in terms of at least one wavelength of the illuminating beam, onto a surface of an object to be measured, wherein a plurality of focal points of a plurality of wavelengths of the illuminating beam form a plurality of chromatic depth measurement ranges, wherein the illuminating beam is reflected by the surface of the object to be measured and forms a monitoring beam, wherein the scanning unit moves along a longitudinal axis of the camera between exactly two positions defined by end stops, from a first end position directly to a second end position, and wherein the scanning unit stepwise displaces the plurality of chromatic depth measurement ranges by a step width that is smaller than or equal to a length of each of the chromatic depth measurement ranges, such that a first chromatic depth measurement range in the first end position of the scanning unit and a second chromatic depth measurement range in the second end position are precisely adjoined in a direction of a measurement depth, or are partially overlapped;

a color sensor that detects the monitoring beam; and a deflector disposed between the chromatic objective and the object to be measured, the deflector not being a part of the scanning unit, and the deflector deflecting the illuminating beam in a direction perpendicular to the longitudinal axis of the camera toward the object to be measured.

2. The handheld dental camera as defined in claim 1, wherein the polychromatic light source comprises a halogen lamp or a xenon gas discharge lamp having a radiation spectrum of from 300 nm to 2000 nm.

3. The handheld dental camera as defined in claim 1, wherein the polychromatic light source comprises a superluminescent diode (SLD).

4. The handheld dental camera as defined in claim 3, wherein the superluminescent diode (SLD) has a radiation spectrum of from 900 nm to 1000 nm.

5. The handheld dental camera as defined in claim 3, wherein the superluminescent diode (SLD) has a radiation spectrum of from 1500 nm to 1650 nm.

6. The handheld dental camera as defined in claim 1, wherein the polychromatic light source comprises a white light light-emitting diode (LED).

7. The handheld dental camera as defined in claim 1, wherein each of the chromatic depth measurement ranges has a length of from 0.5 mm to 5 mm.

8. The handheld dental camera as defined in claim 1, further comprising:

a data processing unit or a connector that connects to the data processing unit, wherein, for each of the chromatic depth measurement ranges, the data processing unit causes a data set to be acquired and saved, and wherein the data processing unit forms an overall 3D data set covering a total depth measurement range by combining each data set for each of the chromatic depth measurement ranges.

9. The handheld dental camera as defined in claim 1, wherein the scanning unit is mechanically moved at a frequency of from 1 Hz to 1000 Hz.

10. The handheld dental camera as defined in claim 1, further comprising:

a mirror disposed between the polychromatic light source and the surface of the object to be measured, wherein the mirror is pivotal about at least an axis perpendicular to the longitudinal axis of the camera such that the illuminating beam is moved stepwise in a direction perpendicular to the longitudinal axis of the camera by stepwise tilting of the mirror.

11. A method for performing three-dimensional (3D), optical measurements using a camera, the method comprising:

emitting an illuminating beam from a polychromatic light source;

focusing the illuminating beam, in terms of at least one wavelength of the illuminating beam, onto a surface of an object to be measured, using a chromatic objective of a scanning unit, wherein a plurality of focal points of a plurality of wavelengths of the illuminating beam form a plurality of chromatic depth measurement ranges, and wherein the illuminating beam is reflected by the surface of the object to be measured and forms a monitoring beam;

detecting the monitoring beam using a color sensor; and moving the scanning unit to exactly two positions defined by end stops, from a first end position directly to a second end position, wherein the chromatic depth measurement ranges are displaced stepwise by a step width that is smaller than or equal to a length of each the chromatic depth measurement ranges by the moving of the scanning unit, such that a first chromatic depth measurement range in the first end position of the scanning unit and a second chromatic depth measurement range in the second end position of the scanning unit are precisely adjoined in a direction of a measurement depth, or are partially overlapped; and deflecting the illuminating beam in a direction perpendicular to a longitudinal axis of the camera toward the object to be measured.

12. The method as defined in claim 11, wherein the polychromatic light source has a spectral range of from 300 nm to 2000 nm.

13. The method as defined in claim 11, wherein the polychromatic light source has a spectral range of from 900 nm to 1000 nm or from 1500 nm to 1650 nm.

14. The method as defined in claim 11, wherein the plurality of focal points of the plurality of wavelengths of the illuminating beam are fanned out such that a length of each of the chromatic depth measurement ranges is from 0.5 mm to 5 mm.

15. The method as defined in claim 11, further comprising:

acquiring and saving within the camera a data set for each of the chromatic depth measurement ranges;

combining each data set and forming a 3D data set of the object to be measured, or transferring each data set to a data processing unit.

16. The method as defined in claim 11, wherein the scanning unit is moved at a frequency of from 1 Hz to 1000 Hz.

17. The method as defined in claim 11, further comprising:

step-wise tilting a pivotal mirror such that the illuminating beam is moved stepwise in a direction perpendicular to the longitudinal axis of the camera.

18. The method as defined in claim 11, wherein the moving of the scanning unit includes measuring each of the chromatic measurement ranges and providing an overall measurement range, in a plurality of steps, wherein the method further comprises moving the scanning unit back to an initial position in a single step after, the moving of the scanning unit, and wherein a measuring cycle of the scanning unit is repeated until a measurement is complete.

19. The method as defined in claim 11,
wherein the moving of the scanning unit includes measuring each of the chromatic measurement ranges and providing an overall measurement range, in a plurality of steps,
wherein the method further comprises moving the scanning unit back to an initial position in a plurality of steps, after the moving of the scanning unit, and
wherein a measuring cycle of the scanning unit is repeated until a measurement is complete.

* * * * *